United States Patent [19]

Katz

[11] 4,263,312
[45] Apr. 21, 1981

[54] SELECTED 5-HYDRAZONO-3-TRICHLOROMETHYL-1,2,4-THIADIAZOLES AND THEIR USE AS FOLIAR FUNGICIDES

[75] Inventor: Lawrence E. Katz, Orange, Conn.

[73] Assignee: Olin Corporation, New Haven, Conn.

[21] Appl. No.: 162,287

[22] Filed: Jun. 23, 1980

[51] Int. Cl.³ .................. A01N 43/82; C07D 285/08
[52] U.S. Cl. .................................. 424/270; 542/417; 548/128
[58] Field of Search ................ 548/128; 424/270; 542/417

[56] References Cited

U.S. PATENT DOCUMENTS 3,324,141  6/1967  Bernstein ............................ 548/128

OTHER PUBLICATIONS

Hickenbottom, Reactions of Organic Compounds, Third Ed., pp. 206-207, (Suffolk, 1957).

Vogel, Practical Organic Chemistry, Third Ed., p. 722, (London, 1961).

Primary Examiner—Alton D. Rollins
Attorney, Agent, or Firm—William A. Simons; Thomas P. O'Day

[57] ABSTRACT

Disclosed are selected 5-hydrazono-3-trichloromethyl-1,2,4-thiadiazole compounds of the formula:

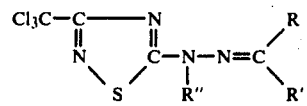

wherein R is a lower alkyl having 1 to 4 carbon atoms, phenyl, and substituted phenyl in which the said phenyl ring substituents are selected from lower alkyl having 1 to 4 carbon atoms, lower alkoxy having 1 to 4 carbon atoms, halo, hydroxy, nitro and mixtures thereof; and R' and R" are individually selected from hydrogen and lower alkyl having 1 to 4 carbon atoms. These compounds are shown to have foliar fungicidal activity.

10 Claims, No Drawings

SELECTED 5-HYDRAZONO-3-TRICHLOROMETHYL-1,2,4-THIADIAZOLES AND THEIR USE AS FOLIAR FUNGICIDES

BACKGROUND OF THE INVENTION

1. Field of the Invention

This invention relates to selected 5-hydrazono-3-trichloromethyl-1,2,4-thiadiazoles and their use as foliar fungicides.

2. Description of the Prior Art

Various 3,5-disubstituted-1,2,4-thiadiazole compounds have been known to possess different types of pesticidal activity such as fungicidal, herbicidal, insecticidal, nematocidal, and the like. For example, U.S. Pat. No. 3,324,141, which issued to Jack Bernstein on June 6, 1967, discloses that various 5-amino or hydrazino-3-trichloromethyl-1,2,4-thiadiazoles are useful as soil fungicides.

BRIEF SUMMARY OF THE INVENTION

The present invention is directed to, as compositions of matter, selected 5-hydrazono-3-trichloromethyl-1,2,4-thiadiazole compounds of the formula:

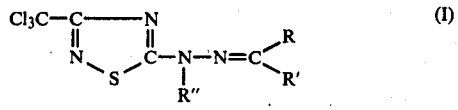

(I)

wherein R is a lower alkyl having 1 to 4 carbon atoms, phenyl, and a substituted phenyl, in which the phenyl ring substituents are selected from lower alkyl having 1 to 4 carbon atoms, lower alkoxy having 1 to 4 carbon atoms, halo such as fluoro, chloro, bromo, iodo, hydroxy, nitro, and mixtures thereof; R' and R" are individually selected from hydrogen and lower alkyl having 1 to 4 carbon atoms. The present invention is also directed toward the use of these compounds as foliar fungicides.

DETAILED DESCRIPTION

The 5-hydrazone compounds of the present invention may be prepared by reacting the corresponding 5-hydrazino-3-trichloromethyl-1,2,4-thiadiazole with a reactive carbonyl compound (e.g., a ketone or aldehyde). This general reaction is illustrated by the following Equation (A) wherein 5-hydrazino-3-trichloromethyl-1,2,4-thiadiazole is reacted with acetone:

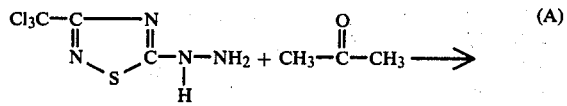

(A)

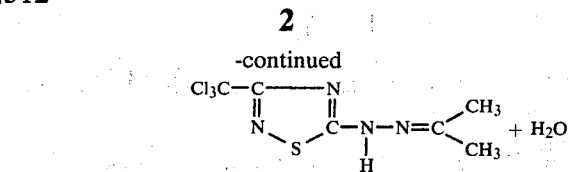

Suitable 3-trichloromethyl-1,2,4-thiadiazole compounds which could be utilized as precursors for the compounds of the present invention include, besides 5-hydrazino-3-trichloromethyl-1,2,4-thiadiazole, mentioned above, the following: 5-(1-methylhydrazino)-3-trichloromethyl-1,2,4-thiadiazole; 5-(1-ethylhydrazino)-3-trichloromethyl-1,2,4-thiadiazole; 5-(1-isopropylhydrazino)-3-trichloromethyl-1,2,4-thiadiazole; 5-(1-n-propylhydrazino)-3-trichloromethyl-1,2,4-thiadiazole; 5-(1-n-butylhydrazino)-3-trichloromethyl-1,2,4-thiadiazole.

The preparation of 5-hydrazino-3-trichloromethyl-1,2,4-thiadiazole is described in U.S. Pat. No. 3,324,141 and is made by reacting 5-chloro-3-trichloromethyl-1,2,4-thiadiazole with hydrazine. These latter two compounds are well known. The 5-substituted hydrazino precursors can be made analogously by reacting 5-chloro-3-trichloromethyl-1,2,4-thiadiazole with the desired substituted hydrazine (i.e., R"HN-NH$_2$).

Suitable reactive carbonyl compounds which can be used as reactants include aldehydes such as acetaldehyde, propionaldehyde, butyraldehyde, 2-methylpropionaldehyde, pivaldehyde, isovaleraldehyde, benzaldehyde, salicylaldehyde, o-anisaldehyde, o-chlorobenzaldehyde, m-chlorobenzaldehyde, p-chlorobenzaldehyde, q-nitrobenzaldehyde, o-tolualdehyde, and 3,4-dichlorobenzaldehyde; and ketones such as acetone, 2-butanone, 3-pentanone and acetophenone. Such aldehydes and ketones are generally available commercially.

Any conventional reaction conditions designed to produce hydrazone compounds may be employed in the synthesis of the present compounds and the present invention is not intended to be limited to any particular reaction conditions. Advantageously and preferably, the reactions are performed with an equimolar amount of the carbonyl compound and the 5-hydrazino-3-trichloromethyl-1,2,4-thiadiazole compound and in the presence of a suitable inert solvent. However, the use of a solvent is only desirable, but not necessary. The reaction temperature and time will both depend upon many factors including the specific reactants used. In most situations, reaction temperatures can advantageously be from about 30° C. to about 100° C. and reaction times from about 0.5 to about 5 hours may be preferred. The product my be recovered from the reaction mixture by any conventional means, for example, filtration, extraction, slurrying with solvent, recrystallization or the like.

It should be noted that while the reaction illustrated by Equation (A) is a preferred method for preparing the compounds of the present invention, other synthetic methods may also be employed.

Several representative compounds of the present invention are included in Table I which follows:

TABLE I

| No. | R | R' | R" | Name of Compound | Name of Carbonyl Precursor |
|---|---|---|---|---|---|
| 1 | CH$_3$ | H | H | 1-(3-trichloromethyl-1,2,4-thiadiazol-5-yl)-2-ethylidenehydrazine | acetaldehyde |
| 2 | CH$_2$CH$_3$ | H | H | 1-(3-trichloromethyl-1,2,4-thiadiazol-5-yl)- | propionaldehyde |

TABLE I-continued

| No. | R | R' | R" | Name of Compound | Name of Carbonyl Precursor |
|---|---|---|---|---|---|
| 3 | $CH_2CH_2CH_3$ | H | H | 1-(3-trichloromethyl-1,2,4-thiadiazol-5-yl)-2-(1-propylidene)hydrazine | butyraldehyde |
| 4 | $CH(CH_3)_2$ | H | H | 1-(3-trichloromethyl-1,2,4-thiadiazol-5-yl)-2-(1-butylidene)hydrazine | 2-methylpropionaldehyde |
| 5 | $C(CH_3)_3$ | H | H | 1-(3-trichloromethyl-1,2,4-thiadiazol-5-yl)-2-[1-(2-methylpropylidene)]hydrazine | pivaldehyde |
| 6 | $CH_2CH(CH_3)_2$ | H | H | 1-(3-trichloromethyl-1,2,4-thiadiazol-5-yl)-2-[1-(2,2-dimethylpropylidene)]hydrazine | isovaleraldehyde |
| 7 | 0-chlorophenyl | H | H | 1-(3-trichloromethyl-1,2,4-thiadiazol-5-yl)-2-[1-(3-methylbutylidene)]hydrazine<br>1-(3-trichloromethyl-1,2,4-thiadiazol-5-yl)-2-o-chlorobenzylidenehydrazine | o-chlorobenzaldehyde |
| 8 | m-chlorophenyl | H | H | 1-(3-trichloromethyl-1,2,4-thiadiazol-5-yl)-2-m-chlorobenzylidenehydrazine | m-chlorobenzaldehyde |
| 9 | p-chlorophenyl | H | H | 1-(3-trichloromethyl-1,2,4-thiadiazol-5-yl)-2-p-chlorobenzylidenehydrazine | p-chlorobenzaldehyde |
| 10 | o-nitrophenyl | H | H | 1-(3-trichloromethyl-1,2,4-thiadiazol-5-yl)-2-o-nitrobenzylidenehydrazine | o-nitrobenzaldehyde |
| 11 | o-methylphenyl | H | H | 1-(3-trichloromethyl-1,2,4-thiadiazol-5-yl)-2-o-methylbenzylidenehydrazine | o-tolualdehyde |
| 12 | o-methoxyphenyl | H | H | 1-(3-trichloromethyl-1,2,4-thiadiazol-5-yl)-2-o-methoxybenzylidenehydrazine | o-anisaldehyde |
| 13 | 3,4-dichlorophenyl | H | H | 1-(3-trichloromethyl-1,2,4-thiadiazol-5-yl)-2-(3,4-dichlorobenzylidene)hydrazine | 3,4-dichlorobenzaldehyde |
| 14 | phenyl | H | H | 1-(3-trichloromethyl-1,2,4-thiadiazol-5-yl)-2-benzylidenehydrazine | benzaldehyde |
| 15 | o-hydroxyphenyl | H | H | 1-(3-trichloromethyl-1,2,4-thiadiazol-5-yl)-2-salicylidenehydrazine | salicylaldehyde |
| 16 | $CH_3$ | $CH_3$ | H | 1-(3-trichloromethyl-1,2,4-thiadiazol-5-yl)-2-isopropylidenehydrazine | acetone |
| 17 | $CH_2CH_3$ | $CH_2CH_3$ | H | 1-(3-trichloromethyl-1,2,4-thiadiazol-5-yl)-2-(3-pentylidene)hydrazine | 3-pentanone |
| 18 | phenyl | $CH_3$ | H | 1-(3-trichloromethyl-1,2,4-thiadiazol-5-yl)-2-(1-phenethylidene)hydrazine | acetophenone |
| 19 | $CH_3$ | $CH_3$ | $CH_3$ | 1-methyl-1-(3-trichloromethyl-1,2,4-thiadiazol-5-yl)-2-isopropylidenehydrazine | acetone |
| 20 | $CH_3$ | H | $CH_3$ | 1-methyl-1-(3-trichloromethyl-1,2,4-thiadiazol-5-yl)-2-ethylidenehydrazine | acetaldehyde |
| 21 | phenyl | $CH_3$ | $CH_3$ | 1-methyl-1-(3-trichloromethyl-1,2,4-thiadiazol-5-yl)-2-(1-phenylethylidene)hydrazine | acetophenone |
| 22 | o-hydroxyphenyl | H | $CH_3$ | 1-methyl-1-(3-trichloromethyl-1,2,4-thiadiazol-5-yl)-2-salicylidenehydrazine | salicylaldehyde |

Also in accordance with the present invention, it has been found that the compounds of Formula I, above may be utilized as effective foliar fungicides. In practicing the process of the present invention, fungi are contacted with a fungicidally effective amount of one or more of these compounds. It is to be understood that the term "fungicidally effective amount" as used in the specification and claims herein is intended to include any amount that will kill or control said foliar fungi when either employed by itself (i.e., in full concentration) or in sufficient concentrations with a carrier or other substance. Of course, this amount may be constantly changing because of the possible variations in many parameters. Some of these may include: the number and type of fungi to be controlled or killed; the type of media to which the present compound can be applied (e.g., seedlings or fully grown plants); degree of effectiveness required; and type of carrier, if any. Generally speaking, applications of an aqueous spray containing at least about 5, more preferably in the range of about 30 to 300, parts per million of the chemical of the present invention may give satisfactory fungi control.

This step of contacting may be accomplished by applying this compound to the fungi themselves, their habitat, dietary media such as vegetation, crops and the like, including many which these pests may attack.

The above-mentioned compounds of the present invention may be formulated and applied by any conventional methods that include using the compound alone or with a carrier or other substances which may enhance the effectiveness of the chemical or facilitate handling. Moreover, the activity of the present compound may be broadened by the addition thereto of other known pesticides such as other fungicides, herbicides, insecticides and the like.

Specific methods of formulating and applying these active compounds include applying them in the form of dusts, dust or emulsion concentrates, wettable powders and concentrates, granulates, dispersions, sprays, solutions and the like.

The dusts are usually prepared by simply grinding together from about 1% to about 15% by weight of the active compound with a finely divided inert diluent such as walnut flour, diatomaceous earth, fullers earth, attaclay, talc or kaolin. Dust concentrates are made in similar fashion excepting that about 16% to about 75% by weight of active compound is ground usually together with the diluent. In practice, dust concentrates are then generally admixed at the site of use with more inert diluent before it is applied to the plant foilage, soil, or animals which are to be protected from fungi attack.

Wettable powders are generally prepared in the same manner as dust concentrates, but usually about 1% to about 10% by weight of a dispersing agent, for example, an alkali metal lignosulfonate and about 1% to about 10% of a surfactant, such as a non-ionic surfactant, are incorporated in the formulation. For application to agronomic crops, shrubs, ornamentals and the like, the wettable powder is usually dispersed in water and applied as a spray.

Emulsifiable liquids may be prepared by dissolving the active compound in an organic solvent, such as xylene or acetone, and admixing the thus formed solution with a surfactant or an emulsifier. The emulsified liquid is then generally dispersed in water for spray or dip application.

It is possible to formulate granulates whereby the active compound is dissolved in an organic solvent and the resulting solution is then applied to a granulated mineral or the like (e.g., bentonite, $SiO_2$, or the like) followed by evaporating off the organic solvent. Granulates can also be obtained by the compacting of the carrier material with the active substance and then reducing this compacted material in size.

Furthermore, the applied formulations of the present invention include other liquid preparations such as dispersions, sprays or solutions. For these purposes, the above-mentioned active compound is normally dissolved in a suitable organic solvent, solvent mixtures or water. As organic solvents, it is possible to use any suitable aliphatic or aromatic hydrocarbon or their derivatives. It is preferred that the solvent be odorless and moreover, be inert to the active compound.

It should be clearly understood that the fungicide formulations, the ingredients which may make up such formulations other than the active compound, the dosages of these ingredients, and means of applying these formulations may include all known and conventional substances, amounts and means, respectively, that are suitable for obtaining the desired fungicidal result. And, therefore, such process parameters are not critical to the present invention.

Fungicides of the present invention may be effective for the control of the broad class of foliar fungi. Specific illustrations of foliar fungi wherein fungicidal activity has been shown include bean rust and cucumber anthracnose.

The following examples further illustrate the present invention. All parts and percentages employed therein are by weight unless otherwise indicated. Yields given are percent molar yields.

EXAMPLE 1

1-(3-Trichloromethyl-1,2,4-thiadiazol-5-yl)-2-Isopropylidenehydrazine

A mixture of 5 ml (3.9 g, 0.068 mole) acetone and 2.4 g (0.01 mole) 5-hydrazino-3-trichloromethyl-1,2,4-thiadiazole was heated 0.5 hour on a steam bath. The solid that was left after evaporation of the excess acetone was recrystallized from ligroin to yield 0.95 g (mp. 75°–77° C.). A second crop of 1.2 g (mp. 66° C.) was obtained after concentration of the solvent. Total yield was 2.15 g (79% yield).

The structure was confirmed via infrared and elemental analysis.

| | Analysis for $C_6H_7N_4Cl_3S$ | | | | |
|---|---|---|---|---|---|
| | C | H | N | Cl | S |
| Calculated: | 26.34 | 2.58 | 20.48 | 38.88 | 11.79 |
| Found: | 26.26 | 2.59 | 20.65 | 38.68 | 11.55 |

EXAMPLE 2

1-(3-Trichloromethyl-1,2,4-thiadiazol-5-yl)-2-(1-Phenethylidene)hydrazine

A mixture of 1.2 g (0.01 mole) acetophenone, 2.4 g (0.01 mole) 5-hydrazino-3-trichloromethyl-1,2,4-thiadiazole, 1 ml hydrochloric acid (conc.), and 100 ml ethanol was heated 5 hours on a steam bath. Water was added and the solution stored in a freezer several days. The resulting solid was removed by filtration to give 2.5 g (73% yield). An analytical sample (mp. 135°–136° C.) was prepared by recrystallization from toluene.

The structure was confirmed via infrared and elemental analysis.

| | Analysis for $C_{11}H_9N_4Cl_3S$ | | | | |
|---|---|---|---|---|---|
| | C | H | N | Cl | S |
| Calculated: | 39.36 | 2.70 | 16.69 | 31.69 | 9.55 |
| Found: | 39.23 | 2.75 | 16.80 | 31.88 | 9.28 |

EXAMPLE 3

1-(3-Trichloromethyl-1,2,4-thiadiazol-5-yl)-2-Salicylidenehydrazine

A mixture of 1.3 g (0.01 mole) salicylaldehyde, 2.4 g (0.01 mole) 5-hydrazino-3-trichloromethyl-1,2,4-thiadiazole, 1 ml hydrochloric acid (conc.), and 100 ml ethanol was heated 5 hours on a steam bath. Water was added and the solution cooled in a freezer several days. The resulting solid was removed by filtration to give 2.8 g (83% yield) (mp. 204°–205° C.).

The structure was confirmed via infrared and elemental analysis.

| | Analysis for $C_{10}H_7N_4Cl_3SO$ | | | | |
|---|---|---|---|---|---|
| | C | H | N | Cl | S |
| Calculated: | 35.57 | 2.09 | 16.60 | 31.51 | 9.50 |
| Found: | 35.48 | 2.19 | 16.43 | 31.50 | 9.25 |

EXAMPLE 4

1-Methyl-1-(3-Trichloromethyl-1,2,4-thidiazol-5-yl)-2-Salicylidenehydrazine

A mixture of 2.50 g (0.01 mole) 5-(1-methylhydrazino)-3-trichloromethyl-1,2,4-thiadiazole and 1.30 g (0.01 mole) salicylaldehyde was stirred. An exothermic reaction ensued and the reaction mixture warmed to 37° C. After 15 minutes ethanol was added and the solid product extracted. The product crystallized and was filtered to yield 2.15 g (61% yield) [mp. 207°–209° C. (dec)].

The structure was confirmed via infrared and elemental analysis.

| | Analysis for $C_{11}H_9N_4Cl_3SO$ | | | | |
|---|---|---|---|---|---|
| | C | H | N | Cl | S |
| Calculated: | 37.57 | 2.58 | 15.93 | 30.25 | 9.12 |
| Found: | 37.85 | 2.55 | 16.15 | 30.57 | 8.89 |

FOLIAR FUNGICIDE SCREEN

The active materials formed in Examples 1, 2, 3 and 4 were then tested for activity as effective fungicides.

A uniform aqueous dispersion of each chemical made in the above examples was first prepared. These dispersions were made by dissolving each chemical in a solution of acetone containing the surfactant TRITON X-155[1] (500 parts per million). Next, this solution was diluted with water (1:9) to obtain a stock solution of 10% by volume acetone and 90% by volume water with 50 ppm TRITON X-155 and the test chemical contained therein. This stock solution was diluted further with water/acetone mix to provide the desired concentration of the test material, if required.

[1] Manufactured by Rohm and Haas of Philadelphia, Pa. and is a polyether alcohol.

The aqueous solutions containing each chemical were applied to various plants according to the methods stated below. These tests were designed to evaluate the ability of the chemical to protect non-infected foliage and eradicate recently established infection against major types of fungi such as rust and anthracnose that attack above-ground parts of plants.

CUCUMBER ANTHRACNOSE

For the primary and secondary screening, two week old cucumber plants were atomized with a suspension of cucumber anthracnose spores (*Collectrotrichium lagenarium*) and placed in a moist chamber at 70° F. for 24 hours. In the primary screening, the young plants were then sprayed while rotating the plants on a turntable with an aqueous solution that contained 260 parts per million by weight of the active chemicals of Examples 1, 2, 3 and 4. Simultaneously, the soil in each pot was drenched with aqueous dispersions of each chemical in the amount of 25 lb/acre. After 5 days, the severity of pustule formation was rated on a scale of 0 (no inhibition) to 10 (complete inhibition). See Table III for the results of these tests.

The same procedure was followed with the compound of Example 3 for secondary screening except lower concentrations of that chemical were employed and the spraying and drenching were separated. See Table III for the results of the secondary screening.

TABLE III

| | FUNGICIDAL ACTIVITY AGAINST CUCUMBER ANTHRACNOSE | | | | | | |
|---|---|---|---|---|---|---|---|
| | Priimary Screening | Secondary Screening | | | | | |
| Compound | 25 lb/acre drench & 260 ppm spray | 12.5 lb/acre drench | 6.3 lb/acre drench | 3.2 lb/acre drench | 130 ppm spray | 65 ppm spray | 33 ppm spray |
| Example 1 | 2 | — | — | — | — | — | — |
| Example 2 | 6 | — | — | — | — | — | — |
| Example 3 | 9 | 0 | 0 | 0 | 10 | 10 | 9 |
| Example 4 | 4 | — | — | — | — | — | — |

BEAN RUST

In primary screening, Pinto beans, which were in 2½ inch pots and 9 to 12 days old, were sprayed while rotating the plants on a turntable with an aqueous solution of each chemical of Examples 1, 2, 3 and 4. The aqueous solutions contained 260 parts per million of each active chemical. Simultaneously, the soil in each pot was drenched with aqueous solutions of each chemical in the amount of 25 lb./acre. After the spray deposit had dried, the plants were atomized with a suspension of uredospores [summer spore stage of bean rust (*Uromyces phaseoli*)] and placed in a moist chamber at 70° F. for 24 hours. After 7 days, the severity of pustule formation was rated on a scale of 0 (no inhibition) to 10 (complete inhibition). See Table II for the results of these tests.

In secondary screening, the same spraying and drenching procedures were followed, except lower concentrations were employed and the spraying and drenching was done separately. After each spraying or drenching, the plants were again atomized with a suspension of uredospores and tested for severity of pustule formation in the same manner. These results are also shown in Table II. The compound of Example 3 was the only one subjected to secondary screening against bean rust.

What is claimed is:

1. A compound of the formula:

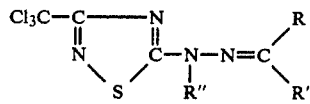

wherein R is a lower alkyl having 1 to 4 carbon atoms, phenyl, and substituted phenyl in which said phenyl ring substituents are selected from lower alkyl having 1 to 4 carbon atoms, lower alkoxy having 1 to 4 carbon atoms, halo, hydroxy, nitro and mixtures thereof; R' and R" are individually selected from hydrogen and lower alkyl having from 1 to 4 carbon atoms.

2. The compound of claim 1 wherein R" is hydrogen.
3. The compound of claim 2 wherein R' is hydrogen.
4. The compound of claim 3 wherein R is lower alkyl having 1 to 4 carbon atoms.
5. The compound of claim 3 wherein R is a substituted phenyl.
6. The compound of claim 5 wherein R is o-hydroxy phenyl.

TABLE II

| | FUNGICIDAL ACTIVITY AGAINST BEAN RUST | | | | | | |
|---|---|---|---|---|---|---|---|
| | Primary screening | Secondary Screening | | | | | |
| Compound | 25 lb/acre drench & 260 ppm spray | 12.5 lb/acre drench | 6.3 lb/acre drench | 3.2 lb/acre drench | 130 ppm spray | 65 ppm spray | 33 ppm spray |
| Example 1 | 10 | — | — | — | — | — | — |
| Example 2 | 10 | — | — | — | — | — | — |
| Example 3 | 10 | 6 | 8 | 6 | 10 | 10 | 10 |
| Example 4 | 4 | — | — | — | — | — | — |

7. The compound of claim 1 wherein R" is lower alkyl having 1 to 4 carbon atoms.

8. The method for controlling fungi which comprises contacting said fungi with a fungicidal amount of a compound of claim 1.

9. The method of claim 8 wherein R" and R' are hydrogen.

10. The method of claim 9 wherein R is a substituted phenyl.

* * * * *